United States Patent [19]

Otten

[11] 4,120,688

[45] Oct. 17, 1978

[54] METHOD OF INCREASING SUCROSE YIELD OF SUGARCANE

[75] Inventor: Geneva Gail Otten, c/o Sharon Woods Technical Center 1150 Reed Hartman Hwy., Cincinnati, Ohio 45241

[73] Assignee: The Proctor & Gamble Company, Cincinnati, Ohio

[21] Appl. No.: 824,468

[22] Filed: Aug. 15, 1977

Related U.S. Application Data

[63] Continuation of Ser. No. 673,315, Apr. 5, 1976, abandoned.

[51] Int. Cl.$^2$ ............................................. A01N 9/36
[52] U.S. Cl. ........................................... 71/86; 71/76
[58] Field of Search ........................................... 71/86

[56] References Cited

U.S. PATENT DOCUMENTS

| | | | |
|---|---|---|---|
| 3,556,762 | 1/1971 | Hamm | 71/86 |
| 3,799,758 | 3/1974 | Franz | 71/86 |
| 3,853,530 | 12/1974 | Franz | 71/76 |
| 3,894,861 | 7/1975 | Hartman | 71/76 |
| 3,909,233 | 9/1975 | Porter | 71/86 |
| 3,961,934 | 6/1976 | Ratts | 71/86 |

*Primary Examiner*—Catherine L Mills
*Attorney, Agent, or Firm*—Ronald L. Hemingway; Richard C. Witte

[57] ABSTRACT

Sucrose yield of sugarcane is increased by treatment prior to harvest with aminomethylphosphonic acid.

8 Claims, No Drawings

METHOD OF INCREASING SUCROSE YIELD OF SUGARCANE

This is a continuation of application Ser. No. 673,315, filed Apr. 5, 1976, now abandoned.

BACKGROUND OF THE INVENTION

This invention relates to increasing the sucrose yield of sugarcane.

Considerable progress has been made in the last several years in this area by improving the varieties being planted, enriching the soil with fertilizers, and irrigating the soil in climates which do not naturally provide sufficient moisture for optimum plant growth. Continuing efforts involve the use of chemicals to modify and control the physiological processes of sugarcane; see particularly U.S. Pat. No. 3,556,762 — N,N-bis(phosphonomethyl glycine), U.S. Pat. No. 3,853,530 — N-(phosphonomethyl glycine), and U.S. Pat. No. 3,909,233 — alkylaminodi(methylphosphonic acid).

It is an object herein to provide a method of increasing the sucrose yield of field grown sugarcane involving utilizing a chemical different from those mentioned above in particular amounts.

This object, other objects, and advantages will be evident from the following detailed description.

DETAILED DESCRIPTION

The above object of increasing the sucrose yield of field grown sugarcane is satisfied within the scope of this invention by applying to the cane at a time prior to harvest, aminomethylphosphonic acid in an amount ranging from about 0.1 pound per acre to about 15 pounds per acre, preferably from about 0.25 pounds per acre to about 10 pounds per acre, most preferably from about 0.5 pounds per acre to about 8 pounds per acre.

Aminomethylposphonic acid has the structural formula

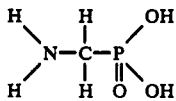

It is readily prepared by reacting triethyl phosphite with N-bromomethylphthalamide and then hydrolyzing using, for example, hydrogen bromide in water. It can also be prepared by the method described in Chavane, *Bull. soc. chim.* 27, p. 774 (1948).

The aminomethylphosphonic acid is applied by established techniques to growing sugarcane plants. In most instances, the time of application referred to above ranges from about 2 weeks to about 10 weeks prior to harvest. Preferably, application is carried out at a time ranging from about 3 weeks to about 9 weeks prior to harvest.

The aminomethylphosphonic acid is preferably formulated in combination with a carrier to provide a composition for application. Such compositions can be liquid (a solution or suspension) or solid (a dust). These compositions are readily applied by conventional methods — for example, spray apparatus or aircraft.

The liquid compositions herein preferably contain water as a carrier. The process for making up such aqueous compositions comprises admixing water and aminomethylphosphonic acid with water being used in an amount such that, for example, application at the rate of about 5 to about 200 gallons of liquid composition per acre will provide the required amount of active (aminomethylphosphonic acid).

Very desirably such liquid composition containing water as a carrier also contains a small amount of non-phytotoxic, that is plant-compatible, surfactant. This surfactant is conveniently added to the water prior to the water being admixed with the aminomethylphosphonic acid. Such surfactant can cause more effective wetting of the sugarcane plant thereby causing more effective utilization of the active. The surfactant can also function as a dispersing or emulsifying agent in the liquid composition.

The surfactants are ordinarily used in an amount based on the weight of the water ranging from about 0.01% by weight to about 5% by weight, preferably ranging from about 0.05% by weight to about 0.5% by weight.

The surfactants for use as described above can be anionic, cationic, nonionic, ampholytic and zwitterionic types.

Examples of suitable anionic surfactants for use herein are the alkali metal (for example, sodium), ammonium and amine salts of fatty alcohol sulfates having from 8–18 carbon atoms in the fatty chain and sodium salts of alkyl benzene sulfonates having from 9 to 15 carbon atoms in the alkyl chain.

Examples of suitable nonionic surfactants are the polyoxyethylene adducts of fatty alcohols having 10 to 18 carbon atoms, and the polyethylene oxide condensates of alkyl phenols wherein the alkyl chain contains from about 6 to 12 carbon atoms and the amount of ethylene oxide condensed onto each mole of alkyl phenol is from about 5 to 25 moles, and the polyethylene oxide condensates of sorbitan esters (for example, surfactants sold under the tradename Tween) wherein the amount of ethylene oxide condensed onto each mole of sorbitan ester is about 10 to 40 moles.

Examples of suitable cationic surfactants are dimethyl dialkyl quaternary ammonium salts wherein the alkyl chains contain from about 8 to 18 carbon atoms and the salt forming anion is a halogen.

Examples of suitable ampholytic surfactants are derivatives of aliphatic secondary or tertiary amines in which one of the aliphatic substituents contains from about 8 to 18 carbon atoms and one contains an anionic water solubilizing group, e.g. sulfate or sulfonate. Specific suitable ampholytic surfactants are sodium-3-dodecylaminopropionate and sodium-3-dodecyl amino propane sulfonate.

Examples of suitable zwitterionic surfactants are derivatives of aliphatic quaternary ammonium compounds in which one of the aliphatic constituents contains from about 8 to 18 carbon atoms and one contains an anionic water solubilizing group. Specific examples of zwitterionic surfactants are 3-(N,N-dimethyl-N-hexadecylammonio)propane-1-sulfonate and 3-(N,N-dimethyl-N-hexadecylammonio)-2-hydroxy propane-1-sulfonate.

Suitable surfactants besides those specifically described above are described in "Detergents and Emulsifiers — 1975 Annual," John W. McCutcheon, Inc.

Nonionic surfactants are preferred, especially nonyl phenol condensed with 5 to 25 moles of ethylene oxide. A very preferred surfactant is sold by Union Carbide under the tradename Tergitol NPX and is nonyl phenol condensed with 10.5 moles of ethylene oxide.

In the above described compositions, a portion (for example, from about 0.1 weight percent to about 10 weight percent) of the water is readily replaced by glycols or lower alcohols. Preferably, the glycol is 1,2-propylene glycol. Other suitable glycols and alcohols include 1,3-propylene glycol, liquid vicinal polyols having a molecular weight below 3000, ethanol, propanol, butanol, and the like.

Other suitable carriers for use in liquid compositions include oils, e.g., hydrocarbons and oil-water emulsions.

Compositions for use herein in the form of dusts can be prepared by grinding and blending the aminomethylphosphonic acid with a solid carrier such as talc, clay or silica.

Example I below illustrates the preparation of aminomethylphosphonic acid by reacting triethyl phosphite with N-bromomethylphthalamide and then hydrolyzing.

EXAMPLE I

N-bromomethylphthalamide (80.1 grams, 0.33 moles) was charged to a 3 neck, 1 liter round bottom flask equipped with distilling head, thermometer, and stirrer. 55.278 grams (0.440 moles) of triethyl phosphite was slowly added with vigorous stirring and heating was commenced. At about 100°–120° C an exotherm began which was controlled at this temperature. The temperature was then raised to 140° C for 3 hours during which time the ethyl bromide side product was removed by distillation. The reaction mixture was then cooled, and the solid precipitate filtered off and washed with hexane. An 88% yield of $C_{13}H_{16}NO_5P$ (mp = 58°–60° C) was realized. The $C_{13}H_{16}NO_5P$ was then refluxed with excess 48% HBr solution overnight. The reaction was then cooled and the product filtered off. The solid was dissolved in a minimum amount of water in a round bottom flask and cooled in an ice bath. Ethylene oxide was slowly added to remove the remaining HBr from the salt. The reaction was exothermic and ethylene oxide addition was continued until the exotherm subsided (indicating completion of HBr removal). Ethanol was then added to the reaction mixture, and the reaction was cooled in an ice bath. The solid product was filtered off and dried (overall yield = 67% aminomethylphosphonic acid).

The above described invention is illustrated in Examples II and III below. The analyses in these examples were carried out by the press method of cane analysis, developed by T. Tanimoto and reported in Hawaiian Planters' Record, Volume 57, pages 133–150. The data are expressed as juice purity and pol percent cane. Pol percent cane is a polarimetric determination and will equal the percentage of sucrose if it is the only substance in the solution which will rotate the plane of polarized light. A determination of pol percent cane is considered by those skilled in the art as an effective means of determining the sucrose content of sugarcane juice.

Examples II and III below are illustrative of the scope of the invention and are not to be construed in any way as limiting the scope of the invention.

EXAMPLE II

For each case denoted in the table below, active as described in the table below was admixed with a small amount of water that contained as a surfactant about 0.25% (by weight of the water) of nonyl phenyl ethoxylated to contain 10.5 moles of ethylene oxide per mole of nonyl phenol. Each resulting admixture is referred to herein as a test material. The test materials were applied to cane plants (14–22 months old) in the field. The application was carried out by hand with a syringe and needle to the top portion (spindle area) of the plants. For each active and level of usage being tested, test material was applied to 15 stalks. Tests were carried out at levels of usage as denoted in the table below. For a level of usage of 2 pounds per acre, about 19 mg. of active was applied per stalk. For a level of usage of 4 pounds per acre, about 38 mg. of active was applied per stalk. For a level of usage of 8 pounds per acre, about 76 mg. of active was applied per stalk. Harvests were made on 5 stalks of each group of 15 stalks 4 weeks after application, 5 weeks after application and 6 weeks after application. The terminal (youngest) 15 joints of each harvested stalk were removed, chopped up, ground and the juice extracted, and the extracts from the 5 harvested stalks combined. Standard analyses as described above were carried out, and the results are set forth in the table below. In that table: aminomethylphosphonic acid (the active of the invention) is denoted AMPA; Polaris is a commercial product and is N,N-bis(phosphonomethyl)glycine; Trysben is a commercial product and is the dimethylamine salt of 2,3,6-trichlorobenzoic acid.

Table

| | | Results of Example II | | | | | |
|---|---|---|---|---|---|---|---|
| | Rate of Application | Harvested 4 Weeks | | Harvested 5 Weeks | | Harvested 6 Weeks | |
| Active Applied | (lbs/acre) | Juice Purity | Pol % Cane | Juice Purity | Pol & Cane | Juice Purity | Pol % Cane |
| AMPA | 2 | 79.96 | 11.52 | 79.13 | 10.47 | 85.24 | 12.71 |
| AMPA | 4 | 78.06 | 10.59 | 75.11 | 11.73 | 80.99 | 11.84 |
| AMPA | 8 | 78.62 | 10.72 | 80.34 | 11.66 | 78.28 | 10.65 |
| Trysben | 4 | 70.51 | 8.44 | 86.50 | 14.08 | 84.13 | 12.48 |
| Polaris | 4 | 80.09 | 11.76 | 79.00 | 11.98 | 83.14 | 12.77 |
| Control | 0 | 70.03 | 8.29 | 73.65 | 9.15 | 73.60 | 8.80 |

The results in the above table indicate the significant activity of aminomethylphosphonic acid in increasing sucrose yield and juice purity.

When in the above example, other surfactants are utilized in place of ethoxylated nonyl phenol, such as sodium dodecyl benzene sulfonate, dimethyl didodecyl ammonium chloride, sodium-3-dodecyl-aminopropionate or 3-(N,N-dimethyl-N-hexadecylammonio) propane-1-sulfonate, significant activity of aminomethylphosphonic acid in increasing sucrose yield and juice purity is obtained.

When in the above example, aminomethylphosphonic acid is applied without surfactant, significant activity in increasing sucrose yield and juice purity is obtained.

EXAMPLE III

The procedure of Example II was followed except that sufficient quantities of each test material were made up and sufficient plants were treated so that data was obtained on plants harvested in each of the fourth, fifth, sixth, seventh, eighth and ninth weeks after application of the test materials. The results are set forth in the table below. In that table: aminomethylphosphonic acid (the active of the invention) is denoted AMPA, and Polaris is a commercial product and is N,N-bis)phosphonomethyl glycine).

ing from about 3 weeks to about 9 weeks prior to harvest.

3. A method as recited in claim 2 in which the aminomethylphosphonic acid is applied in an amount

Table

Results of Example III

| Active Applied | Rate of Application (lbs/acre) | Harvested 4 weeks | | Harvested 5 weeks | | Harvested 6 weeks | | Harvested 7 weeks | | Harvested 8 weeks | | Harvested 9 weeks | |
|---|---|---|---|---|---|---|---|---|---|---|---|---|---|
| | | Juice Purity | Pol % Cane | Juice Purity | Pol % Cane | Juice Purity | Pol % Cane | Juice Purity | Pol % Cane | Juice Purity | Pol % Cane | Juice Purity | Pol % Cane |
| AMPA | 2 | 73.03 | 8.50 | 70.11 | 7.87 | 79.20 | 10.80 | 72.39 | 8.51 | 77.29 | 9.54 | 82.68 | 12.01 |
| AMPA | 4 | 71.36 | 8.34 | 83.81 | 11.70 | 79.51 | 10.64 | 81.55 | 11.36 | 81.40 | 10.75 | 71.22 | 8.27 |
| Polaris | 4 | 73.60 | 9.15 | 76.97 | 9.69 | 78.73 | 10.92 | 77.77 | 9.80 | 80.68 | 11.06 | 76.05 | 11.29 |
| Control | 0 | 68.15 | 7.49 | 78.40 | 10.16 | 73.42 | 9.09 | 70.47 | 8.02 | 81.52 | 11.13 | 66.86 | 7.22 |

The results in the above table indicate the significant activity of aminomethylphosphonic acid in increasing sucrose yield and juice purity.

The term "control" is used herein to mean that no active was applied.

The invention may be embodied in other specific forms without departing from the spirit or essential characteristics thereof. In view of the variations that are readily understood, to come within the limits of the invention, such limits are defined by the scope of the claims.

I claim:

1. A method for increasing the sucrose yield of field grown sugarcane comprising applying to the cane at a time ranging from about 2 weeks to about 10 weeks prior to harvest aminomethylphosphonic acid in an amount ranging from about 0.1 pounds per acre to about 15 pounds per acre.

2. A method as recited in claim 1 in which the aminomethylphosphonic acid is applied at a time ranging from about 2 weeks to about 10 weeks prior to harvest.

3. A method as recited in claim 2 in which the aminomethylphosphonic acid is applied in an amount ranging from about 0.25 pounds per acre to about 10 pounds per acre.

4. A method as recited in claim 3 in which the aminomethylphosphonic acid is applied in an amount ranging from about 0.5 pounds per acre to about 8 pounds per acre.

5. A method as recited in claim 4 in which the aminomethylphosphonic acid is applied in an aqueous composition.

6. A method as recited in claim 5 in which said aqueous composition comprises non-phytotoxic surfactant in an amount based on the weight of the water ranging from about 0.01% by weight to about 5% by weight.

7. A method as recited in claim 6 in which said aqueous composition comprises surfactant in an amount based on the weight of the water ranging from about 0.05% by weight to about 0.5% by weight.

8. A method as recited in claim 7 in which the surfactant is nonyl phenol condensed with 10.5 moles of ethylene oxide per mole of nonyl phenol.

* * * * *